US005321759A

United States Patent [19]

Yuan

[11] Patent Number: 5,321,759

[45] Date of Patent: Jun. 14, 1994

[54] ACTIVE NOISE CONTROL SYSTEM FOR ATTENUATING ENGINE GENERATED NOISE

[75] Inventor: Yi Yuan, Warren, Mich.

[73] Assignee: General Motors Corporation, Detroit, Mich.

[21] Appl. No.: 875,897

[22] Filed: Apr. 29, 1992

[51] Int. Cl.[5] ........................ A61F 11/06; H03B 29/00

[52] U.S. Cl. ........................ 381/71

[58] Field of Search ........................ 381/71, 94, 86, 72

[56] References Cited

U.S. PATENT DOCUMENTS

| | | | |
|---|---|---|---|
| 4,480,333 | 10/1984 | Ross | 381/71 |
| 4,506,380 | 3/1985 | Matsui | 381/71 |
| 4,683,590 | 7/1987 | Miyoshi et al. | 381/71 |
| 4,689,821 | 8/1987 | Salikuddin et al. | 381/71 |
| 4,805,733 | 2/1989 | Kato et al. | 181/206 |
| 4,878,188 | 10/1991 | Ziegler | 364/724.01 |
| 5,010,576 | 4/1991 | Hill | 381/71 |
| 5,022,082 | 6/1991 | Eriksson et al. | 381/71 |
| 5,063,598 | 11/1991 | Geddes | 381/71 |
| 5,140,640 | 8/1992 | Graupe et al. | 381/71 |
| 5,146,505 | 9/1992 | Pfaff et al. | 381/71 |
| 5,170,433 | 12/1992 | Elliott et al. | 381/71 |

FOREIGN PATENT DOCUMENTS 2201858 9/1988 United Kingdom .

*Primary Examiner*—Curtis Kuntz
*Assistant Examiner*—Ping W. Lee
*Attorney, Agent, or Firm*—Jimmy L. Funke

[57] ABSTRACT

An active noise control (ANC) system is disclosed for attenuating engine generated noise that contains at least one sinusoidal noise component having an amplitude and frequency that vary with changes in engine rotational speed. The ANC system includes a means for generating at least one generator output signal that contains one or more sinusoidal signal components, where the frequency of each signal component corresponds to the frequency of a respective noise component. A separate control signal having an amplitude that varies with engine rotational speed is generated to correspond with each generator output signal. Each generator output signal is then multiplied by its respective control signal to produce a corresponding filter input signal. Each filter input signal passes to a respective adaptive filter, where it is filtered to produce a corresponding filter output signal according to the adjustable filtering characteristics of the adaptive filter. Noise canceling waves are generated by a noise canceling actuator in response to each filter output signal, and the canceling waves are superimposed with the undesirable noise generated by the engine. The level of residual noise resulting from this superposition is sensed, and an error signal is developed to represent the residual noise level. The filtering characteristics of each adaptive filter are adaptively adjusted based upon the error signal to minimize the residual noise level. In the preferred embodiment, each control signal has its amplitude determined in accordance with a respective predetermined function based upon the sensed engine rotational speed, and each predetermined function is correlative of the amplitude behavior of those noise components corresponding to the signal components contained in the generator output signal that is multiplied by the respective control signal.

6 Claims, 6 Drawing Sheets

ACTIVE NOISE CONTROL SYSTEM FOR ATTENUATING ENGINE GENERATED NOISE

BACKGROUND OF THE INVENTION

This invention relates to active noise control (ANC) systems that are used for attenuating undesirable noise, and more particularly, to ANC systems utilized for canceling noise produced by internal combustion engines, where the noise contains multiple closely spaced sinusoidal frequency components having amplitudes and frequencies that vary in relationship with the rotational speed of the engine.

Conventional active noise control (ANC) systems attenuate undesirable noise by producing and superimposing noise canceling waves, which are substantially equal in amplitude and frequency content, but shifted 180 degrees in phase with respect to the undesirable noise. As used in the present specification and the appended claims, the term noise is hereby defined to include both acoustic waves and mechanical vibrations propagating from a noise source.

Recently, ANC has been accomplished by employing modern digital signal processing and adaptive filtering techniques. Typically, an input sensor is utilized to derive a signal representative of the undesirable noise generated by a source. This signal is then applied to the input of an adaptive filter and is transformed by the filter characteristics into an output signal used for driving a cancellation transducer or actuator such as an acoustic speaker or electromechanical vibrator. The speaker or vibrator produces canceling waves or vibrations that are superimposed with the undesirable noise generated by the source. The observed or residual noise level resulting from the superposition of the undesirable noise and the canceling waves is then measured with an error sensor, which develops a corresponding error feedback signal. This feedback signal provides the basis for modifying the characteristics of the adaptive filter to minimize the overall level of the observed or residual noise.

Such systems have been successfully applied to attenuate, for example, repetitive noise generated by fans or electric motors and random noise propagating down heating and air conditioning ducts. The nature of acoustic and vibrational noise generated by an internal combustion engine differs quite significantly from the nature of the repetitive or random noise encountered in the past.

Engine generated noise generally contains a large number sinusoidal noise components having amplitudes and frequencies that are functionally related to the rotational speed of the engine. These frequency components have been found to be the even and odd harmonics of the fundamental frequency of engine rotation (in revolutions per second), as well as half-order multiples or sub-harmonics interposed between the even and odd noise harmonics. Consequently, at low engine speeds, the difference in frequency between adjacent noise components (i.e. those noise components immediately preceding or following each other in the frequency domain) can become quite small, for example, as little as 5 Hz at engine idle. In addition, the amplitude, frequency, and phase of the engine generated noise components can vary quite rapidly in response to changes in engine rotational speed brought about by acceleration or deceleration of engine. Also, engines having differing numbers of cylinders generate noise characterized by different dominant frequency components due to the difference in their firing frequencies. Finally, engine generated noise can have different amplitude and frequency characteristics depending upon the particular type of noise, for example, acoustic noise propagating from the engine intake or exhaust system, or mechanical vibrations produced by operation of the engine, which are transmitted to a vehicle frame.

Consequently, there exists a need for a flexible active noise control system that can be tailored to effectively attenuate undesirable noise containing multiple sinusoidal frequency components, particularly in applications where the difference in frequency separating these noise components is small in comparison with the values of their individual frequencies, and where the amplitude, frequency, and phase of the sinusoidal noise components can change quite abruptly, such as in noise generated by an internal combustion engine during periods of rapid engine acceleration or deceleration.

SUMMARY OF THE INVENTION

The present invention provides an active noise control (ANC) system for attenuating engine generated noise, where the noise contains at least one sinusoidal noise component having an amplitude and frequency that vary in relation to changes in engine rotational speed. The ANC system includes a means for generating at least one generator output signal that contains one or more sinusoidal signals each having a frequency corresponding to the frequency of a respective noise components. A separate control signal having an amplitude that depends upon engine rotational speed is produced to correspond with each generator output signal. Each generator output signal is then multiplied by its respective control signal to produce a corresponding filter input signal. Each filter input signal passes to a respective adaptive filter, where it is filtered to produce a corresponding filter output signal according to the adjustable filtering characteristics of the adaptive filter. Noise canceling waves are generated by a noise canceling actuator in response to each filter output signal, and the canceling waves are superimposed with the undesirable noise generated by the engine. The level of residual noise resulting from this superposition is sensed, and an error signal is developed to represent the residual noise level. The filtering characteristics of each adaptive filter are adaptively adjusted based upon the error signal to minimize the residual noise level.

When the engine noise contains multiple sinusoidal noise components, it is preferable that the sinusoidal signal components contained in the generator output signals be partitioned according to the amplitude behavior of their corresponding noise components with changes in engine rotational speed. The amplitude of each control signal can then be determined in accordance with a respective predetermined function based upon the sensed engine rotational speed, where each predetermined function is made correlative of the amplitude behavior of those noise components corresponding to the signal components contained in the respective generator output signal that is multiplied by the control signal. This effectuates a predetermined scaling of the amplitude of each generator output signal based upon the engine rotational speed, which has been found to significantly improve the ability of the ANC system to attenuate engine noise components having amplitudes that behave in a similar fashion with changes in engine rotational speed. This is because the amplitudes of the sinusoidal signal components entering the adaptive filters are scaled to more closely match the amplitude behavior of their corresponding engine noise components. As a consequence, the adaptive filters require less time to converge in adapting the filter output signal amplitudes to achieve an acceptable level engine noise attenuation.

According to another aspect of the invention, the rotational position of the engine in an operating cycle is sensed, and engine rotational speed is derived by determining the time rate of change of the engine rotational position. Each generator output signal can then be conveniently derived from a respective predetermined schedule of values based upon the sensed angular rotational position of the engine in the operating cycle.

The invention claimed in the present application is disclosed in conjunction with two additional inventions that may be implemented for improving the performance of active noise control systems used for attenuating engine generated noise. One of these additional inventions is associated with implementing the ANC system so that sinusoidal signal components corresponding to noise components that are adjacent with respect to frequency are contained in different ones of the generator output signals. The other additional invention is related to the scaling of filter adaptation factors based upon engine rotational acceleration and/or engine rotational speed. These inventions are respectively claimed in related U.S. Patent Applications having Attorney Docket Numbers G-9338 and G-10099, which were filed contemporaneously with the present application, and are also assigned to the same assignee.

These and other aspects and advantages of the invention may be best understood by reference to the following detailed description of the preferred embodiments when considered in conjunction with the accompanying drawings.

DESCRIPTION OF THE PREFERRED EMBODIMENTS

Figure 1:
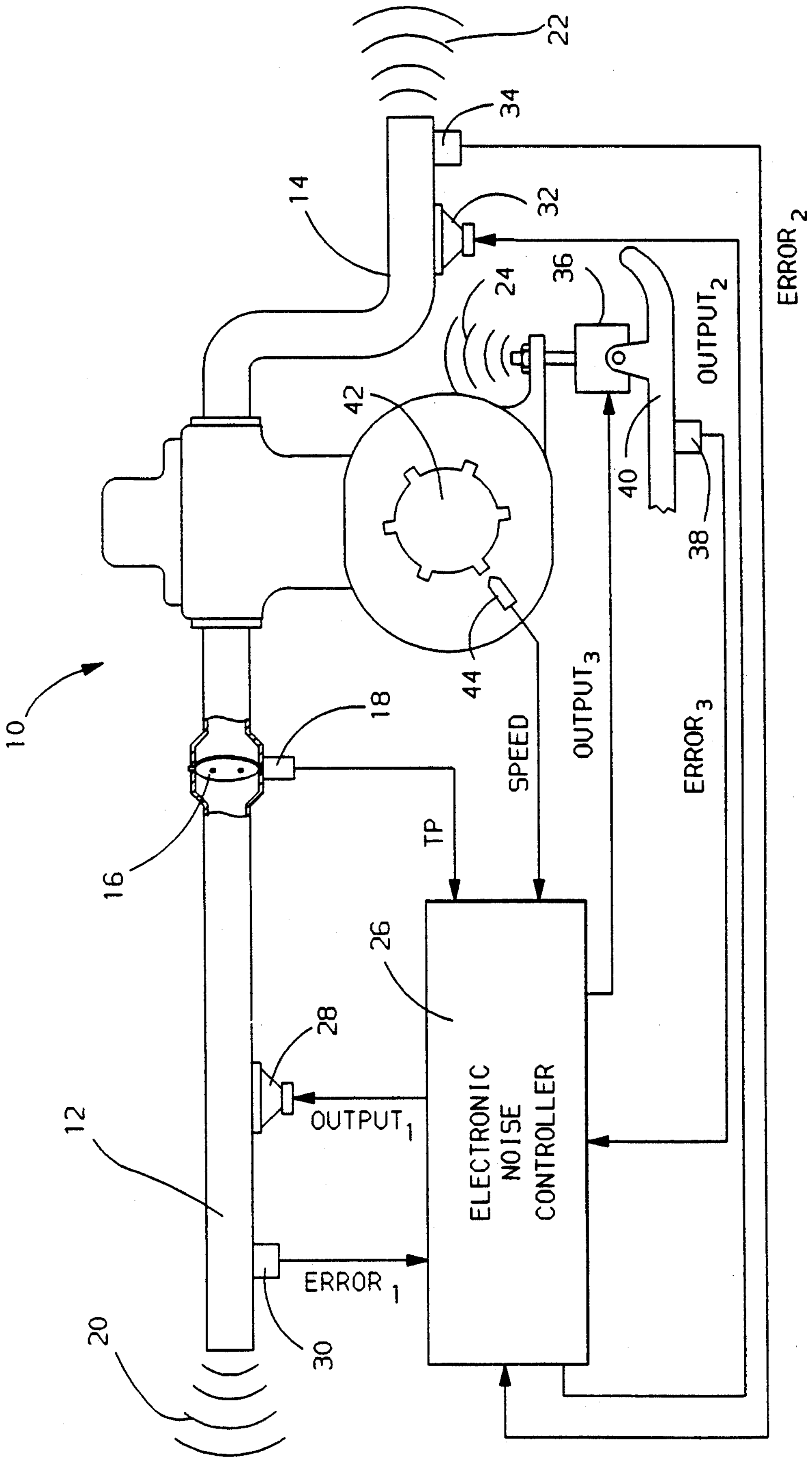
FIG. 1 is a schematic diagram of an active noise control system having a multi-channel electronic noise controller for attenuating different forms of undesirable noise generated by an engine.

Referring to FIG. 1, there is shown schematically an internal combustion engine, generally designated as 10, with its associated air intake system 12 and exhaust system 14. A rotatable throttle valve 16 is included within the air intake system 12 for regulating air flow to the engine 10. Also shown are two sensors generally associated with the electronic control of engine performance. The first is a standard throttle position sensor 18, such as a potentiometer, which is connected to throttle valve 16 for developing an electrical signal TP related to the degree or percent of throttle valve opening. The second is a conventional engine rotation sensor, in this case shown as a toothed wheel 42 mounted on the engine crankshaft, and an electromagnetic sensor 44 that produces a SPEED signal having pulses corresponding to the movement of teeth on wheel 42 past sensor 44. As shown, toothed wheel 42 has six symmetrically spaced teeth, which produce six equally spaced pulses in the engine SPEED signal for every complete revolution of the engine 10. This particular toothed wheel is merely exemplary, and wheels having different numbers of teeth can be just as easily used, or alternatively, any other known type of sensor or transducer capable of producing outputs pulses in response to the rotation of the engine can be employed.

During the operation of engine 10, acoustic pressure waves are generated and propagate away from the engine through the ducts and tubes forming the air intake and exhaust systems. Eventually, these pressure waves propagate from openings in the intake and exhaust systems as observable engine induction noise 20 and exhaust noise 22. In addition, the engine generates undesirable noise in the form of mechanical vibrations 24, which are transferred to a mounting frame 40 used to support engine 10.

In general, engine generated noise contains a large number of sinusoidal components having amplitudes and frequencies that vary in relation to the rotational speed of the engine. The frequencies of these components have been found to be even, odd, and half-order multiples of the fundamental frequency of rotation of the engine (in revolutions per second). Consequently, at low engine speeds, the difference in frequency between adjacent noise components can become quite small (in the order of 5 Hz) making them difficult to distinguish. In addition, the amplitude and frequency of the engine generated noise components can vary quite rapidly in response to abrupt changes in engine acceleration or deceleration brought about by variations in engine loading or operator demand for engine output power. Also, engines having differing numbers of cylinders generate noise characterized by different dominant frequency components, due to the difference firing frequencies. Finally, the type of engine noise can have different frequency components depending upon the source of the engine noise, i.e. acoustic waves propagating from the engine intake or exhaust systems, or mechanical waves or vibrations transmitted from the operating engine to the vehicle frame.

Consequently, to be practical an active noise control system for canceling different forms of engine generated noise must be capable of selectively attenuating a large number of noise frequency components, some of which can have relatively small differences in frequency. It is also necessary that such a system have the ability to accurately track and adapt to rapid variations in the amplitude, frequency, and phase of engine generated noise components that have been found to occur at different rotational speeds and/or during abrupt acceleration or deceleration of the engine.

As will now be described, the present invention is directed toward providing an active noise control system having the above mentioned capabilities. The general components of such an active noise control system are shown in FIG. 1. For illustrating a few of the many different applications that are possible, electronic noise controller 26 is shown as a multi-channel device having three separate channels, with each channel operating to attenuate one of the different forms of engine noise discussed above, i.e. intake induction noise, exhaust noise, and vibrational noise.

One channel of the noise controller 26 is utilized to attenuate the engine generated induction noise propagating inside the air intake system 12. As will be described, the electronic noise controller 26 generates a canceling $OUTPUT_1$ waveform based upon the input engine SPEED signal. This $OUTPUT_1$ signal drives a canceling actuator 28, which in this case is an audio speaker, which produces canceling acoustic waves that are superpositioned with the engine generated induction noise. Sensor or transducer 30, in this case an acoustic microphone, is positioned in the air intake system 12 to measure the level of the residual or attenuated induction noise remaining in the air intake system 12 after the superposition of the canceling acoustic waves. Sensor 30 develops an $ERROR_1$ signal representing the level of the residual induction noise, which is directed back to the induction noise channel of the electronic noise controller 26. This $ERROR_1$ signal provides the basis for minimizing the observed or residual induction noise 20 propagating out of engine intake system 12.

A second channel of the noise controller 26 is employed to cancel exhaust noise. The operations described above for the induction noise application are duplicated, except that a noise canceling signal $OUTPUT_2$ is produced to drive the exhaust noise canceling actuator 32 (in this case an acoustic speaker) positioned to generate and propagate acoustic waves in the exhaust system, and an error sensor 34 (in this case an acoustic microphone) for developing an $ERROR_2$ signal representing the level of residual exhaust noise propagating from engine 10.

Similarly, for canceling engine generated vibrational noise 24, a third channel of the noise controller 26 produces noise canceling signal $OUTPUT_3$ to drive an electromechanical vibrator 36, shown here as being disposed between engine 10 and mounting frame 40. Electromechanical vibrator 36 may be any type of actuator known to those skilled in the art of active noise control, which is capable of producing the required out-of-phase canceling vibrations for superposition with the engine generated vibrations transmitted to mounting frame 40. For example, a commercially available Model LAV 2-3/5-6 actuator manufactured by Aura, Inc could be used as shown in FIG. 1, or alternatively, a Model 203B Shaker supplied by Ling Electronics, Inc. could be mounted on frame 40 for producing the required out-of-phase canceling vibrations. For this channel, an error feedback signal $ERROR_3$ representing the residual vibrations transferred to the mounting frame 40 is developed by an error sensor 38, which in this case is a standard accelerometer attached to the mounting frame 40.

Figure 2:
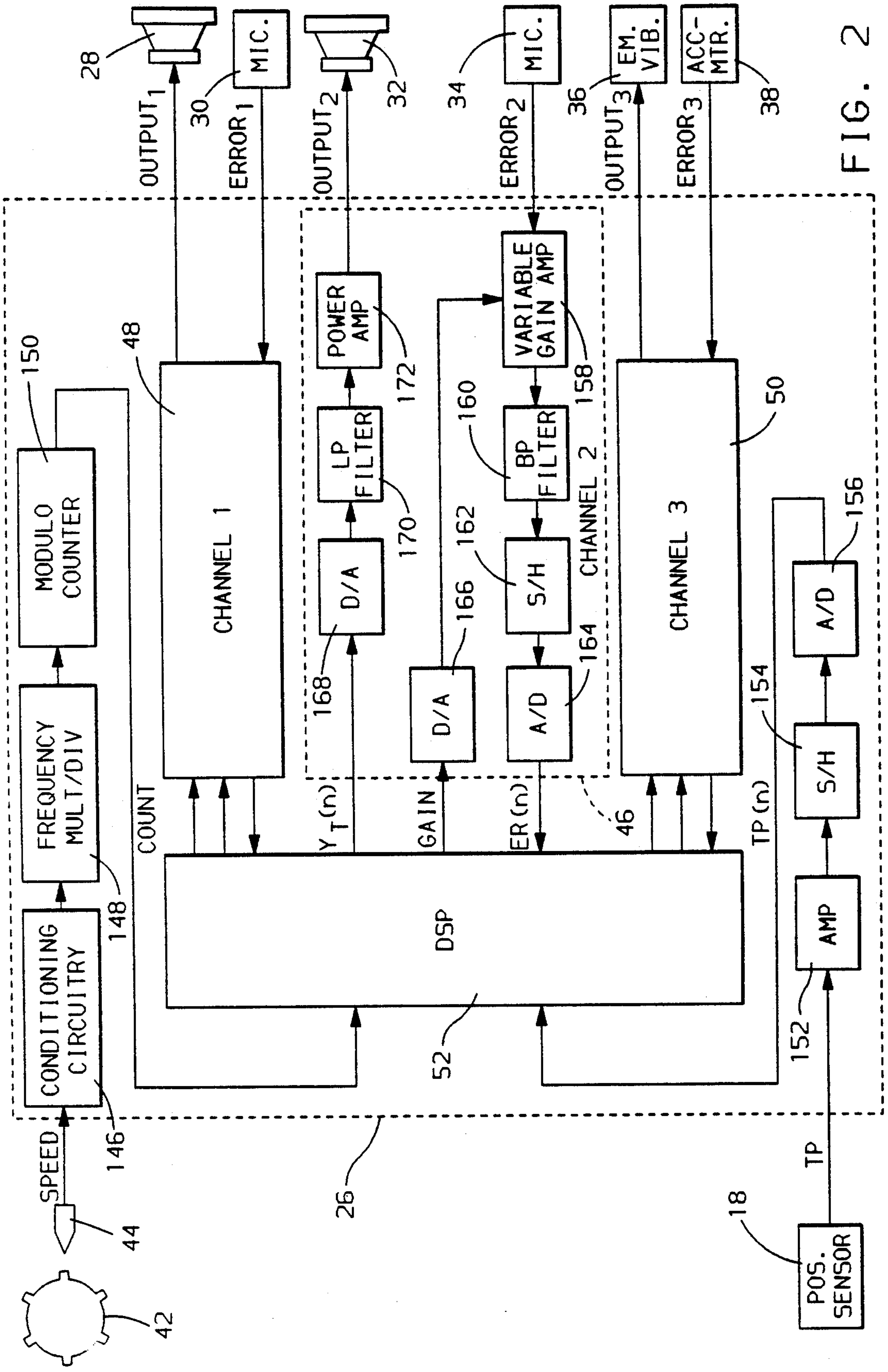
FIG. 2 is a block diagram representative of the electronic components employed in implementing the noise controller shown in FIG. 1.

Referring now to FIG. 2, the electronic circuitry within the noise controller 26 will now be described in terms of a block diagram containing standard well known electronic components present in the second channel 46 in the noise controller. The first and third channels, 48 and 50 respectively, contain the same components adapted to provide the appropriate input and output levels for their particular cancellation actuators and error sensors, and accordingly, only the components within the second channel will be described to avoid unnecessary duplication in the specification.

It will be recognized that the implementation shown in FIG. 2 is merely exemplary and is not intended to limit the present invention, since other variations in the hardware are possible, as evident in the numerous patents, texts, and publications directed toward the subject of active noise control, see for example, "Hardware and Software Considerations for Active Noise Control", M. C. Allie, C. D. Bremigan, L. J. Eriksson, and R. A. Greiner, 1988, IEEE, CH 2561-9/88/0000-2598, pp. 2598-2601.

One of the principal electronic component in the preferred implementation of noise controller 26 is a digital signal processor (DSP) designated by numeral 52. Digital signal processors are commercially available, such as the Motorola 56000, and typically include a central processing unit (CPU) for carrying out instructions and arithmetic operations, random access memory (RAM) for storing data, a programmable read only memory (PROM) for storing program instructions, and clock or timing circuitry, used for example, to establishing the data sampling rate at which the DSP operates For the multiple channel operation illustrated in FIGS. 1 and 2, the DSP 52 is programmed to function as one or more adaptive filters for each channel and it operates sequentially to perform the necessary steps or operations for each channel within the established data sampling rate (2.5 KHz in the present embodiment).

As described previously, an indication of the angular rotational position of the engine is preferably provided to the electronic noise controller 26 by the SPEED signal developed by the electromagnetic speed sensor 44. The SPEED signal contains pulses generated by the movement of toothed wheel 42 past electromagnetic sensor 44. After entering the noise controller 26, the SPEED signal is passed to standard conditioning circuitry 146, where the pulses are shaped or squared up into a format compatible with the digital circuitry that follows. These formatted digital pulses represent a measure of the angular rotation of the crankshaft and are passed to a standard frequency multiplier/divider circuit 148, which generates a fixed or predetermined number of pulses during one complete rotational cycle of the engine. The pulses from the frequency multiplier/divider 148 are then counted by a conventional modulo counter 150, to provide a digital output signal designated as COUNT. This digital COUNT signal is then used as a reference input signal to the DSP 52 representing the time-varying degree of engine rotation through a complete engine cycle. As such, it will be recognized that the value of the COUNT signal will be functionally related to the frequencies of sinusoidal noise components generated by the engine.

In general, the number of teeth on wheel 42, the frequency multiplier/divider, and the modulo counter are selected to provide an integer count ranging in value from 0, to a maximum value of MAX, each time the engine completes a cycle. A complete cycle in a four-stroke engine being two full revolutions of the engine crankshaft. The value of COUNT then represents the time-varying angular rotational position of the engine in an operating cycle or the fractional portion of an engine cycle completed at any given time (the cycle position). Based upon the value of the COUNT reference input signal, the DSP 52 is able to generate signals containing different sinusoidal components having frequencies that correspond to those of the sinusoidal noise components generated by the engine.

In addition to the SPEED signal, the other analog signals directed to the noise controller 26 are sampled at the rate established by DSP 52 and digitized for further use within the DSP 52. Sets of sample values for the digitized input signals are retained in the RAM memory of DSP 52 for use in computing sample values for digital output signals in accordance with the programmed adaptive filters in each channel. The computed digital output signal samples from DSP 52 are then converted into analog form and appropriately amplified to drive the channel cancellation actuators.

With regard to analog inputs signals directed to the electronic noise controller 26, the analog throttle position signal TP from sensor 18 is first passed through amplifier 152, and then converted into a digital input signal TP(n) for the DSP 52 by the action of sample and hold circuit 154 and analog-to-digital converter 156. TP(n) then represents the nth or most recent digitized sample value for the analog throttle position signal TP, TP(n−1) represents the digitized sample value for TP obtained during the previous sampling period, and likewise for earlier sample values of the throttle position signal. Although not required to implement the present invention, the digitized throttle position signal is shown as an input to the DSP 52 for completeness, since it provides an indication of engine loading, and may be used to improve ANC performance as described in co-pending U.S application Ser. No. 07/565,395 filed Aug. 10, 1990 and assigned to the same assignee as the present application.

The analog $ERROR_2$ developed by microphone sensor 34 is first amplified by a variable gain amplifier designated as 158 and then passed through a bandpass filter 160 having, for example, a passband from approximately 20 to 700 Hz in this particular implementation. Bandpass filter 160 acts as an anti-aliasing filter and removes any direct current from the amplified $ERROR_2$ signal. The filtered $ERROR_2$ signal is then applied to sample and hold circuit 162, which acts in conjunction with analog-to-digital converter 164 to provide a digitized sample ER(n) of the analog $ERROR_2$ signal to the DSP 52, where as stated previously, n represents the nth or most re sampled value.

Based upon the value of the digitized ER(n) sample, the DSP 52 supplies a digital GAIN signal to digital-to-analog converter 166, which in turn controls the gain of amplifier 158 to maintain the amplitude of the amplified analog $ERROR_2$ signal within upper and lower limits determined by the input capability of sample and hold circuit 162 and analog-to-digital converter 164. This form of automatic gain control is well known in the art and is commonly used in DSP and microprocessor interfacing circuitry when digitizing an analog signal having an amplitude that can vary over a large dynamic range, such as the ERROR2 signal in the present embodiment.

Sequential digital sample values for an output noise canceling signal . . . , $Y_T(n-2)$, $Y_T(n-1)$, and $Y_T(n)$ are computed by the DSP 52 in accordance with the above described input signals and the characteristics of the adaptive filters programmed into the DSP 52 for the second channel. These digital output samples are directed to digital-to-analog converter 168, where a corresponding analog waveform is produced. The analog waveform is then passed through lowpass filter 170, which has an upper cutoff frequency of approximately 700 Hz in this particular implementation. The lowpass filter acts as a smoothing filter to remove any high frequency components introduced by the digital-to-analog conversion process. Next, the filtered analog waveform is amplified by power amplifier 172 to produce the final output noise canceling waveform designated as $OUTPUT_2$. The $OUTPUT_2$ signal drives the cancellation actuator (speaker) 32 to produce the noise canceling waves that are superimposed with and attenuate the undesirable engine exhaust noise.

Depending upon the amplitude of the noise being attenuated, it may be desirable to prevent the amplitude of the noise canceling waveform from becoming saturated or clipped at an upper limit related to the physical size of the cancellation actuator. An approach that may be used to prevent such clipping or saturation of the output noise canceling waveform is described in U.S. patent application Ser. No. 07/842,880 filed Feb. 26, 1992, which is a continuation-in-part of U.S. patent application Ser. No. 07/565,395 filed Aug. 10, 1990, and U.S. patent application Ser. No. 07/620,801 filed Dec. 3, 1990, now abandoned.

Figure 3:
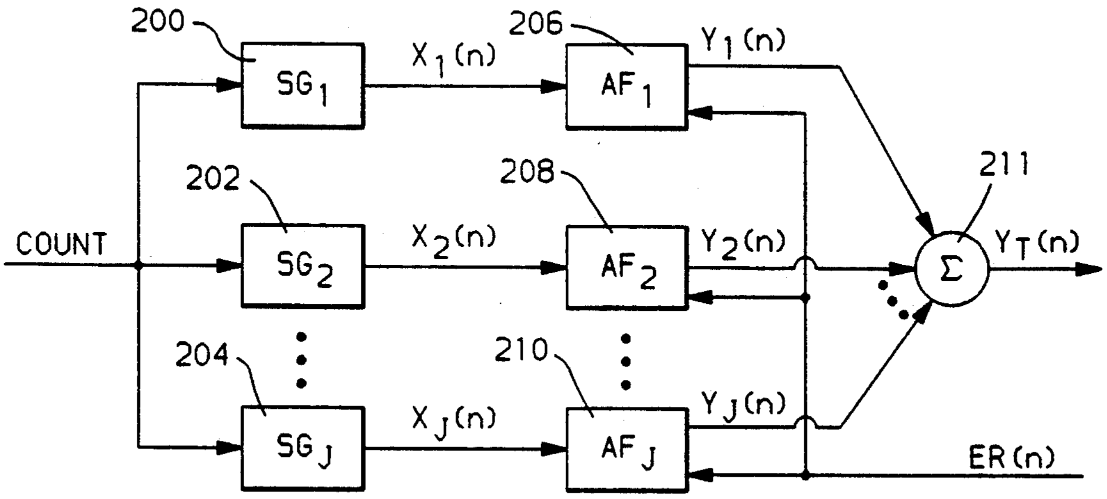
FIG. 3 is a block diagram model containing a parallel configuration of signal generator and adaptive filter pairs representing signal processing steps that are programmed into and carried out by the digital signal processor of FIG. 2 for active noise control.

Referring now to FIG. 3, there is shown a block diagram model for a generalized parallel configuration of signal generator and adaptive filter pairs that represents signal processing steps programmed into and carried out by the DSP 52 for the second channel of the noise controller 26. It will be recognized that the other channels of noise controller 26 can be programmed to have similar configurations and signal processing steps.

In general, the parallel configuration of FIG. 3 is shown to include a total of J signal generators $SG_1$, $SG_2$, . . . , and $SG_J$, designated by the respective numerals 200, 202, and 204, and J correspondingly paired adaptive filters $AF_1$, $AF_2$, . . . , and $AF_J$, designated respectively as 206, 208, and 210. Based upon the value of the common input reference signal COUNT, each signal generator $SG_j$ synthesizes a sampled output signal $X_j(n)$, which is then used as input for the corresponding paired adaptive filter $AF_j$, where $j=1, 2, \ldots,$ and J. Each adaptive filter $AF_j$ operates on its respective sampled input signal $X_j(n)$ to produce a sampled digital filter output signal $Y_j(n)$. All of the sampled filter output signals $Y_j(n)$ from the adaptive filters $AF_j$ are directed to a signal summer 211, where they are added together to produce digital samples for the final output noise canceling signal $Y_T(n)$ generated by the DSP 52. Each adaptive filter $AF_j$ is also provided with digital sample values ER(n) representing the second channel feedback error signal $ERROR_2$ (see FIG. 2), so that the characteristics of the J adaptive filters can be adapted to reduce the magnitude of the $ERROR_2$ signal and the corresponding level of residual exhaust noise 22 propagating from the engine 10 (see FIG. 1).

The operation of each of the signal generators will now be described in terms of a jth signal generator $SG_j$, where j can have the values of $j=1, 2, \ldots,$ or J. In general, the jth generator $SG_j$ produces a value for its sampled output signal $X_j(n)$ based on the current value of the COUNT reference input signal in accordance with the following equation:

$$X_j(n) = \sum_{m=1}^{M} B_{mj} \sin(m\ q\ \text{COUNT}), \tag{1}$$

where the $B_{mj}$ term represents the amplitude of the mth sinusoidal signal component in a summation that can contain a total of M such components, and q is a conversion constant given by $q=2\pi/(MAX+1)$, where MAX is the maximum count reached by the COUNT signal from the modulo counter 150, before it resets to zero to restart counting. It will be recognized that one or more sinusoidal signal components can be removed from the above summation by setting their respective amplitudes to zero, i.e. the mth sinusoidal component can be removed from the signal $X_j(n)$ produced by the jth signal generator $SG_j$ by merely setting $B_{mj}=0$ to eliminate any contribution from that component.

It will also be recognized that since COUNT ranges in value from 0 to MAX for each complete engine cycle (two revolutions in a four stroke engine), the frequencies of the sinusoidal components in above equation (1) will be functionally related to, and synchronized with the rotational frequency of the engine (in revolutions per second). For example, if the engine rotates at a frequency of $f_0$ revolutions per second (engine RPM/60), then the frequency of the mth sinusoidal component in the summation of equation (1) is given by $f_m=mf_0/2$. Consequently, by setting the appropriate amplitude terms $B_{mj}$ equal to zero, the sampled generator output signal $X_j(n)$ produced by the jth signal generator $SG_j$ can be easily adjusted to contain sinusoidal components having frequencies at selected even, odd, and/or half-order multiples of the fundamental frequency of rotation of the engine $f_0$.

In what follows, it will be understood that when a set of sequential sample values for a digitized signal, such as the output signal for the jth signal generator $X_j(n-N_j+1), \ldots, X_j(n-2), X_j(n-1)$, and $X_j(n)$, are retained in the DSP 52 RAM memory, prior to storing a newly generated sample value in the memory location corresponding to the nth sample value $X_j(n)$, the previous stored value for $X_j(n)$ will be shifted downward and stored as the next earlier sample value $X_j(n-1)$, and likewise for all earlier sample values down to the last retained sample in the sequence $X_j(n-N_j+1)$.

Figure 4:
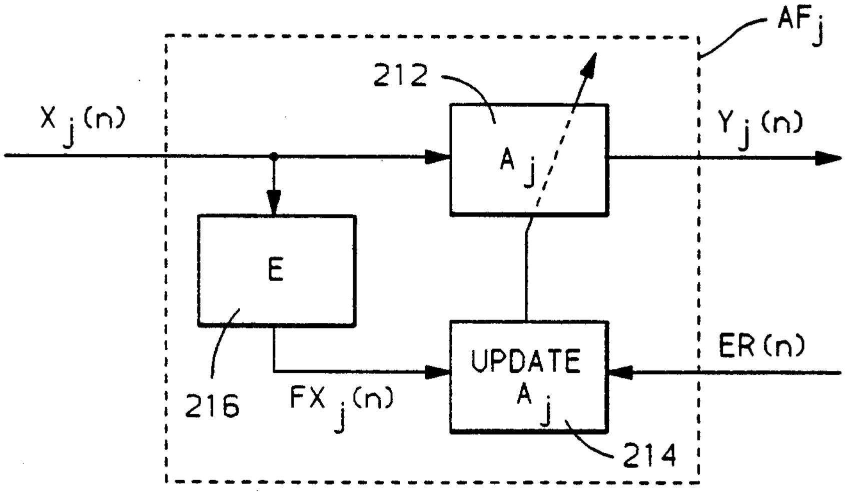
FIG. 4 is a block diagram representing the modeling components contained within each of the adaptive filters $AF_j$ shown in FIG. 3, where $j=1, 2, \ldots, J$.

The preferred form for each of the adaptive filters in FIG. 3 will now be described in terms of a general model representing the jth adaptive filter $AF_j$ as shown in FIG. 4, which is commonly known as the filtered-X LMS configuration. The components within each adaptive filter $AF_j$ include a transversal digital filter $A_j$ 212, which filters or transforms the filter input signal, in this case the sampled signal $X_j(n)$ synthesized by the jth signal generator $SG_j$, to produce a sampled filter output signal $Y_j(n)$ according to the equation:

$$Y_j(n) = \sum_{i=0}^{N_j-1} W_{ij}(n)\, X_j(n-i), \tag{2}$$

where the set of $W_{ij}(n)$ terms represent the most recently computed adaptive filter weighting coefficients for the transversal filter $A_j$ 212, and $N_j$ represents the number of taps or size of transversal filter $A_j$, and also the number of samples of the jth signal generator output $X_j(n)$ retained in memory for computing the current sample value for the filter output signal $Y_j(n)$. In general, the transversal filter $A_j$ 212 in each adaptive filter $AF_j$ can have a different number of taps $N_j$, however, the number of taps for a particular filter must be equal to at least twice the number of sinusoidal signal components selected to be synthesized by that filter's corresponding signal generator $SG_j$ so that the transversal filter will be capable of forming a separate passband for each synthesized sinusoidal signal component.

After each new sample value for the filter output signal $Y_j(n)$ is computed according to equations (2), the weighting coefficients $W_{ij}(n)$ for each transversal filter $A_j$ are updated, as indicated by the UPDATE $A_j$ block 214, to minimize the value of the sampled error signal ER(n). This updating is preferably accomplished using the leaky least-mean-square (LMS) algorithm, although any other known algorithm for adapting filter weighting coefficients to minimize the error signal could be used. The UPDATE $A_j$ block has two inputs, the first being the current sample value for the error signal ER(n), and the second being a filtered sequence of sample values designated as $FX_j(n)$, which are derived by passing samples of the filter input signal (here the jth signal generator output $X_j(n)$) through an auxiliary compensation E filter 216. This auxiliary filtering process gives rise to the filtered-X nomenclature associated with this type of adaptive filter.

The preferred leaky LMS algorithm for updating each of the filter weighting coefficients from the present value $W_{ij}(n)$, to the value $W_{ij}(n+1)$ for use during the next sampling interval, is given by:

$$W_{ij}(n+1) = g_j W_{ij}(n) - \mu_j ER(n) FX_j(n), \tag{3}$$

where $g_j$ is known as the filter leakage factor generally having a value in the range of $0<<g_j<1$, and $\mu_j$ is known as the filter convergence factor generally having a value in the range of $0<\mu_j<<1$. The convergence factor $\mu_j$ is related to the rate at which the filter output signal samples represented by $Y_j(n)$ converges to values that minimizes the sampled error signal ER(n). The leakage factor $g_j$ prevents the accumulation of digital quantization error that typically occurs when using a digital signal processor having fixed point arithmetic capabilities, such as the Motorola 56000 DSP. In applications where the frequency and amplitude of the noise are stationary or slowly varying with respect to time, $g_j$ and $\mu_j$ are conventionally fixed at constant values.

The sequence of sample values for the $FX_j(n)$ signal required by equation (4) are obtained by filtering the sequence of sample output values $X_j(n)$ from the jth signal generator $SG_j$ with an auxiliary compensation E filter 216 according to the following equation:

$$FX_j(n) = \sum_{i=0}^{N_E-1} E_i\, X_j(n-i), \tag{4}$$

where the $E_i$ terms for i=0, 1, . . . ,and $N_E-1$ represent the fixed weighting coefficients for the transversal compensation E filter 216, with $N_E$ representing the number of E filter taps. As described in "An Analysis of Multiple Correlation Cancellation Loops with a Filter in the Auxiliary Path", D. R. Morgan, IEEE Transactions on Acoustic Speech Speech Signal Processing, Vol. ASSP-28, No. 4, 1980, pp. 454–467, a compensation filter such as the E filter 216 is typically used to compensate for the delay and distortion introduced by components in the error path of the ANC system. This error path typically includes the channel cancellation actuator and the associated output circuitry within noise controller 26; the error sensor and the associated error input circuitry within noise controller 26; and the characteristics of the physical path between the channel cancellation actuator and error sensor, over which the engine noise propagates.

Figure 5:
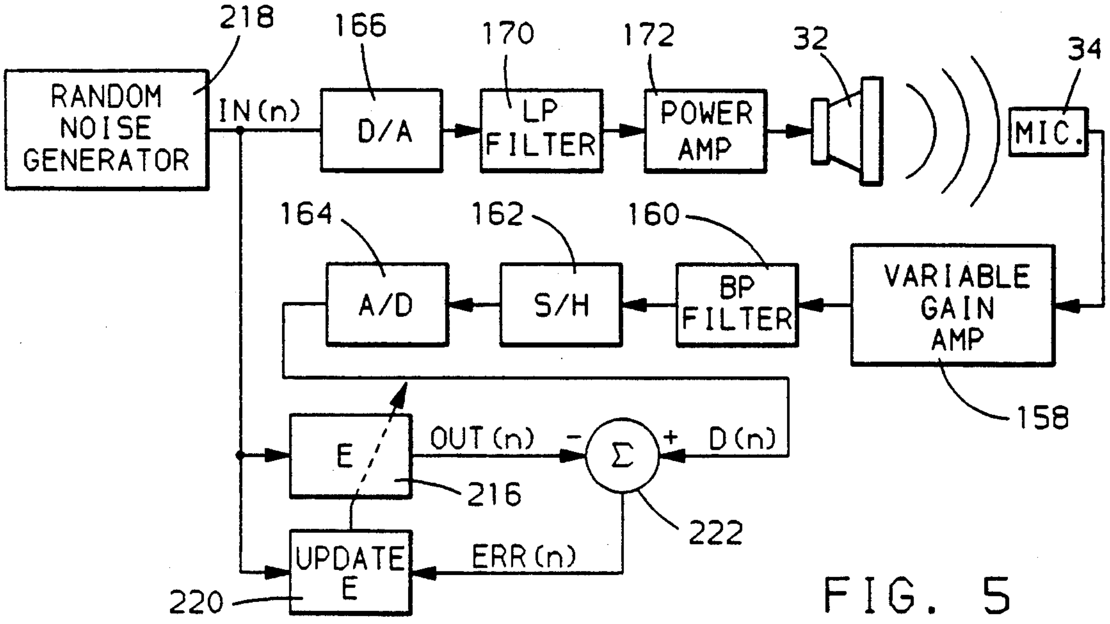
FIG. 5 is a block diagram illustrating an off-line training process for the compensation E filter included within each of the adaptive filters $AF_j$ illustrated in FIG. 4.

Referring now to FIG. 5, there is shown a schematic diagram representing a process that can be used for off-line training each compensation E filter 216. In this process, the E filter is trained (i.e. its weighting coefficients are adjusted) to have a transfer function equivalent to the combined electrical components in the error path of the second channel between the DSP digital output signal $Y_T(n)$ and digital input error signal ER(n). When training the E filter, the noise cancellation actuator 32 and the error sensor 34 must remain at the same locations as when they are used for attenuating noise, to assure that the characteristics of the propagation path between the cancellation actuator 32 and error sensor 34 remain constant.

During the training process, a conventional random noise generator 218 is used to generate a sequence of random signal values designated as IN(n). The random signal samples are directed as input to the auxiliary compensation E filter 216, and are also passed through the components of the error path to produce a corresponding sequence of samples designated as D(n). In passing over the error path, the IN(n) samples are subjected to the same electronic components as are output $Y_T(n)$ samples and the resulting ER(n) samples of the second channel 46 of the noise controller 26 of FIG. 2.

For the training configuration shown in FIG. 5, the expression associated with operation of the digital compensation E filter 216, and the algorithm associated with its UPDATE E adaptation block 220, are given by:

$$\mathrm{OUT}(n) = \sum_{i=0}^{N_E-1} E_i(n)\,\mathrm{IN}(n-i), \text{ and} \tag{5}$$

$$E_i(n+1) = g_E\,E_i(n) + \mu_E\,ERR(n)\,\mathrm{IN}(n), \tag{6}$$

where $g_E$ and $\mu_E$ are set at approximately $g_E=0.99998$ and $\mu_E 0.001$, OUT(n) represents sample values output by the digital E filter 216, and the ERR(n) samples are produced as output from signal summer 222 and are given by:

$$ERR(n)=D(n)-OUT(n), \tag{7}$$

where D(n) represents the sample values derived from the channel error sensor 34. With this off-line training process, the weighting coefficients of the digital E filter 216 are adaptively updated to minimize the ERR(n) values. The adaptive modeling procedure is complete when the variable weighting coefficients $E_i(n)$ sufficiently converge to fixed values. These fixed values then correspond to the fixed weighting coefficients $E_i$ used in implementing the E filter 216. When the adaptive modeling procedure is complete, the transfer function of the digital E filter 216 duplicates that of the combined components in the channel error path; and it is used for filtering the sampled $X_j(n)$ signal to produce filtered samples for the $FX_j(n)$ signal input to the UPDATE $A_j$ block 214 in FIG. 4. As is well known, filtering the samples of the $X_j(n)$ signal in this manner compensates for distortion and delay introduced by the error path components and improves the stability and rate of convergence of the adaptive filter $AF_j$.

As indicated in FIG. 4, the same E filter 216 is preferably used with each adaptive filters $AF_j$, with j=1, 2, . . . ,J, since it provides a broad band characterization of the error path over a range in frequency which embraces the expected variations in frequency of the engine noise components. Also, using the same compensation E filter for each adaptive filter $AF_j$ provides advantages in that the implementation is simplified and RAM storage space is conserved; however, different E filters could be used with each adaptive filter if desirable or advantageous for the particular application.

When employed in ANC systems, the above described parallel configuration of signal generators $SG_j$ and paired adaptive digital filters $AF_j$ provides distinct advantages over conventional adaptive filtering approaches, particularly when the difference in frequency between adjacent noise components (i.e. those noise components immediately preceding or following each other in the frequency domain) become relatively small.

First, the required number of parallel signal generator and adaptive filter pairs in the configuration can be less than the total number of noise frequency components being attenuated, since each signal generator is capable of producing or synthesizing more than one of the sinusoidal signal components corresponding in frequency with the noise components. More importantly, each signal generator in the parallel configuration can be programmed to produce a set of sinusoidal signal components having frequencies corresponding to non-adjacent noise frequency components. This aspect is significant because the difference in frequency between successive sinusoidal signal components filtered by any one adaptive filter is effectively increased, which enables a reduction in the number of filter taps without adversely affecting filtering performance. As will be recognized by those skilled in the art, the filter convergence factor can be enlarged to increase the rate of convergence as the number of filter taps decreases without degrading filter stability. Also, as the number of filter taps is reduced, quantities known as the LMS algorithm excess means square error and computational round off error decrease to improve filter accuracy. Consequently, significance improvements in the filter accuracy and the rate of response to fluctuation in noise amplitude, frequency, and phase can be realized by employing the above described parallel configuration of signal generators and correspondingly paired adaptive filters in ANC systems in the above described manner.

Figure 6:
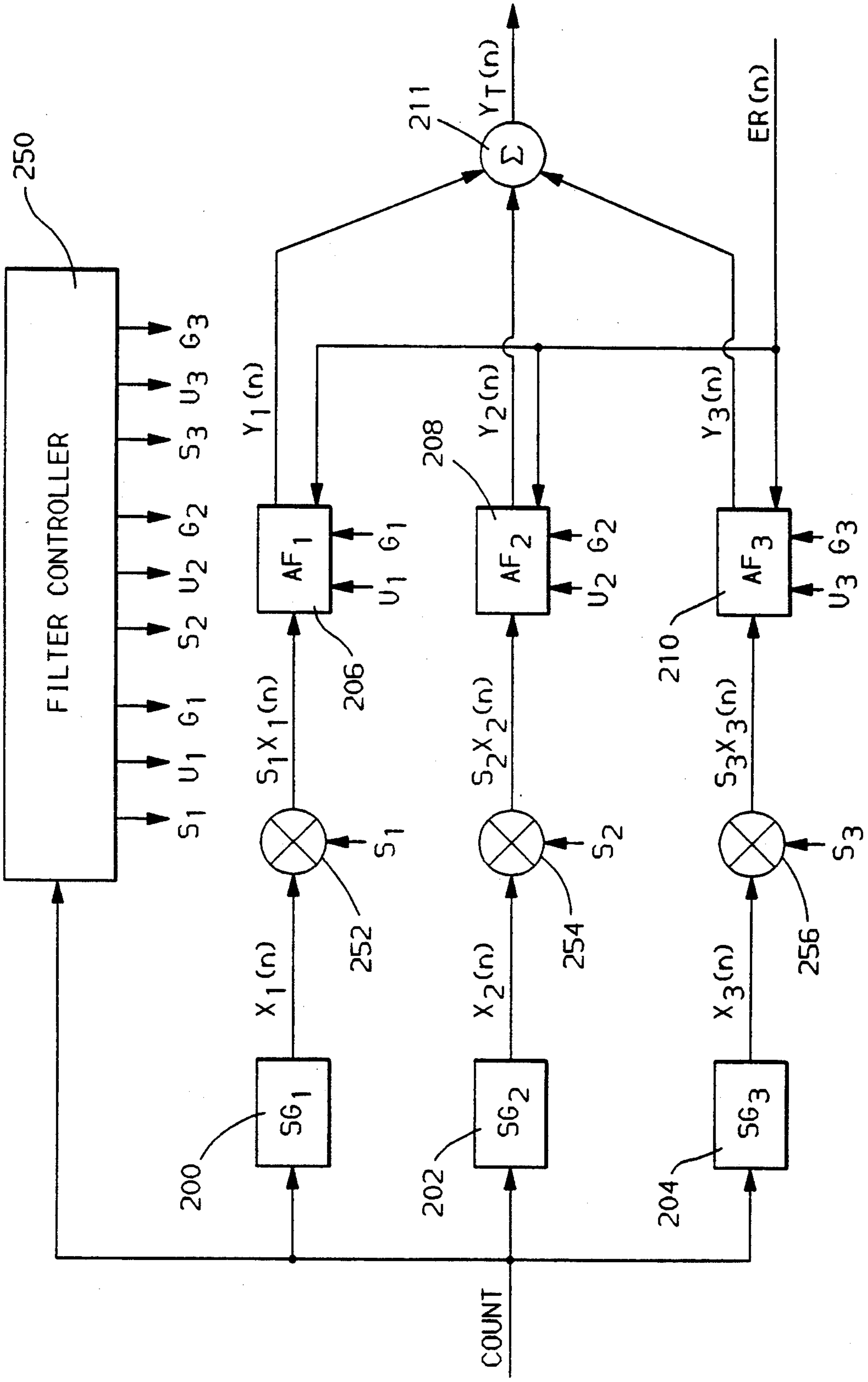
FIG. 6 is a block diagram for a model programmed into the digital signal processor, which includes a filter controller for use in conjunction with the parallel configuration of signal generator and adaptive filter pairs employed for attenuating engine generated exhaust noise.

Referring now to FIG. 6, there is shown a block diagram for a model representing signal processing steps programmed into the DSP 52 of the electronic noise controller 26 (see FIG. 2) for attenuating engine generated exhaust noise The model includes a filter controller, which operates in conjunction with the above described configuration of parallel signal generator and adaptive filter pairs. For this particular application and type of noise, it has been found that three parallel signal generator and adaptive filter pairs (i.e. $J=3$) are sufficient to achieve an acceptable degree of attenuation of the engine exhaust noise. It has also been found that each transversal filter $A_j$ and each compensation filter E provides satisfactory performance with sixty-four taps, i.e. $N_j=N_E=64$; however, it will be understood that a larger or smaller number of filter taps could be used for any of the filters depending upon the required degree of noise attenuation and any limitations on the amount of memory available for storage in the DSP 52.

In selecting the frequency make-up of the set of sinusoidal signal components synthesized by any one signal generator, the measured variations in amplitude and frequency of the exhaust noise components with changes in engine speed was considered in conjunction with separating those sinusoidal signal components that corresponds to exhaust noise components having adjacent frequencies.

The following predominant characteristics of the engine exhaust noise were identified during the operation of engine 10, which for the present embodiment was a 4.9 liter, 8 cylinder engine: (1) as the engine was operated over its range of possible rotational speeds, the dominant noise components in the exhaust noise (those having significant amplitudes) were found to have the frequencies of $mf_0/2$, where m has integer values ranging from 2 to 16, and $f_0$ is the fundamental frequency of rotation of the engine in Hz (i.e. revolutions per second or RPM/60); (2) the exhaust noise component having a frequency of $4f_0$ was found to have a significant amplitude at rotational speeds between 600 and 2200 RPM; (3) engine noise components having frequencies of $f_0$, $2f_0$, $3f_0$, $5f_0$, $6f_0$, $7f_0$, and $8f_0$, were found to have significant amplitudes when the engine was operated above 1400 RPM; and (4) engine noise components having frequencies of $3f_0/2$, $5f_0/2$, $7f/2$, $9f_0/2$, $11f_0/2$, $13f_0/2$, and $15f_0/2$, were found to have significant amplitudes when the engine was operated above 2500 RPM.

In addition to identifying the above characteristics, it was also found that the amplitude and frequency of the exhaust noise components can vary quite rapidly in response to abrupt changes in engine rotational speed during rapid acceleration or deceleration of the engine. As will be explained subsequently, additional improvements in performance of the ANC system can be realized by programming each signal generator to synthesize a distinct set of signal components having frequencies corresponding to those noise components that behave in the same manner over a particular range of engine rotational speed. As will be explained, additional improvements in the performance of the ANC system can be realized by programming each signal generators to synthesize sinusoidal signal components that correspond in frequency with engine noise components having similar amplitude behavior at different engine rotational speed.

In the block diagram model illustrated in FIG. 6, signal generator $SG_1$ was programmed to synthesize the sinusoidal signal component having a frequency corresponding to noise component frequency of $4f_0$. This was done by assigning the value of zero to all $B_{ml}$ amplitude terms in equation (1) for the $SG_1$ signal signal generator, except for the $B_{81}$ amplitude term associated with the sinusoidal signal component having the frequency of $4f_0$. The signal generator $SG_2$ was programmed to synthesize sinusoidal signal components corresponding to engine noise components having the non-adjacent frequencies of $f_0$, $2f0$, $3f_0$, $5f_0$, $6f_0$, $7f_0$, and $8f_0$, that were found to have significant amplitudes when the engine 10 was operated above 1400 RPM. This was accomplished by assigning values of zero to those amplitude terms $B_{m2}$ corresponding to frequencies not produced by the second signal generator $SG_2$, i.e. $B_{m2}=0$, for m=1, 3, 5, 7, 8, 9, 11, 13, and 15.

The third signal generator $SG_3$ was programmed to synthesize sinusoidal signal components corresponding to engine noise components having the non-adjacent frequencies of $3f_0/2$, $5f_0/2$, $7f_0/2$, $9f_0/2$, $11f_0/2$, $13f_0/2$, and $15f_0/2$ that were found to have significant amplitudes when the engine was operated above 2500 RPM. Again, this was accomplished by assigning values of zero to those amplitude terms $B_{m3}$ corresponding to those frequencies not produced by the third signal generator $SG_3$, i.e. $B_{m3}0$, for m=2, 4, 6, 8, 10, 12, 14, and 16.

Those amplitude terms $B_{mj}$ corresponding to the frequencies of sinusoidal components that are produced by the signal generators can be assigned values of 1.0, or they can be assigned relative values obtained by averaging the measured amplitudes of the corresponding engine noise frequency components over the range of possible engine rotational speeds.

The above manner of partitioning not only separates the sinusoidal components so that no one signal generator is required to synthesize any sinusoidal components that correspond to engine noise components having adjacent frequencies, but it also enables the implementation of a control strategy, whereby the operation of the configuration of parallel signal generator and adaptive filter pairs can be regulated to compensate for the rapid variations in the amplitude and frequency of engine generated noise components when engine rotational speed changes.

As indicated in FIG. 6, the control of each signal generator and paired adaptive filter in the parallel configuration is carried out by a filter controller 250 and three signal multiplier 252, 254, and 256, each being interposed between one of the signal generator outputs and the input of the corresponding paired adaptive filter. During each new sampling interval, filter controller 250 develops sets of digital values for the output control signals $S_j$, $U_j$, and $G_j$ that are directed to control the operation of each signal generator $SG_j$ and corresponding paired adaptive filter $AF_j$ (where j=1, 2, and 3). These output control signals are derived in the filter controller 250 based upon information provided by digital COUNT signal.

The control signals $S_j$ are applied to the respective signal multipliers 252, 254, and 256 to effectuate amplitude scaling of each signal generator input signal $X_j(n)$ for each adaptive filter scaled input signal $S_jX_j(n)$ for each adaptive filter $AF_j$. It will be understood that the above described equations (2) and (4) will continue to apply, except that it will be understood that each occurrence of the expression $X_j(n)$ will be replaced by its corresponding amplitude scaled counterpart $S_jX_j(n)$.

The control signals $U_j$ and $G_j$ are applied directly to each of the respective adaptive filters $AF_j$ to modify the updating or adaptation process. This is accomplished by adjusting or scaling the values of the leakage factor $g_j$ and convergence factor $\mu_j$ in the algorithm used to update each adaptive filter, based upon the current values of the control signals $U_j$ and $G_j$. Consequently, the leakage and convergence factors are allowed to have variable values in according to the following expressions:

$$g_j = G_j g_0, \text{ and} \quad (8)$$

$$\mu_j = U_j \mu_{0j}, \quad (9)$$

where $g_0$ and $\mu_{0j}$ are set at constant values and the control signals $G_j$ and $U_j$ effectuate a scaling of these constant values to provide the scaled filter adaptation factors $g_j$ and $\mu_j$. For example, $g_0=0.99998$, $\mu_{01}=0.001$, and $\mu_{02}=\mu_{03}=0.01$, provided stable filter operation in the present embodiment, but it will be recognized that the values selected for the $\mu_{0j}$ terms will differ for different applications depending upon factors such as the average power contained in the filter input signals, the number of adaptive filter taps, and the electrical characteristics of hardware components such as the actuators and transducers outside the DSP.

The values for the control signals $S_j$, $U_j$, and $G_j$ are determined by filter controller 250 as a function of the engine rotational speed in RPM and/or the engine rotational acceleration expressed in RPM/second (or RPM/s). Engine rotational speed for the current sampling interval can be computed by filter controller 250 using the expression:

$$SP(n) = K1(COUNT - COUNT_{-1}), \quad (10)$$

where K1 is a scaling constant, COUNT represent the value of the modulo counter 150 during the current sampling interval, and $COUNT_{-1}$ represents the stored value of the modulo counter during the previous sampling interval. Although equation (10) provides an acceptable estimate for the actual engine rotational speed, it has been found that a more accurate representation is obtained by averaging a few of the most recently computed sample values for SP(n). Consequently, the preferred expression for computing engine rotational speed for the current or nth sampling interval is given by:

$$\text{SPEED}(n) = (1/N) \sum_{i=0}^{N-1} SP(n-i), \quad (11)$$

where N represents the number of samples of SP(n) that are averaged, for example, N=32 in the present embodiment. The rotational acceleration of the engine for the current sampling interval is computed by use of the expression:

$$\text{ACCEL}(n) = K2(\text{SPEED}(n) - \text{SPEED}(n-1)), \quad (12)$$

where K2 represents an additional scaling constant, SPEED(n) represent the rotational speed of the engine for the current sampling interval computed in accordance with equation (10), and SPEED(n−1) represents the stored rotational speed of the engine found during the previous sampling interval. It will be recognized that the scaling constants K1 and K2 are selected so that equations (10), (11), and (12) provide the correct values for the engine rotational speed and acceleration for the sampling interval associated with the sampling rate established by the DSP 52.

Figure 7A:
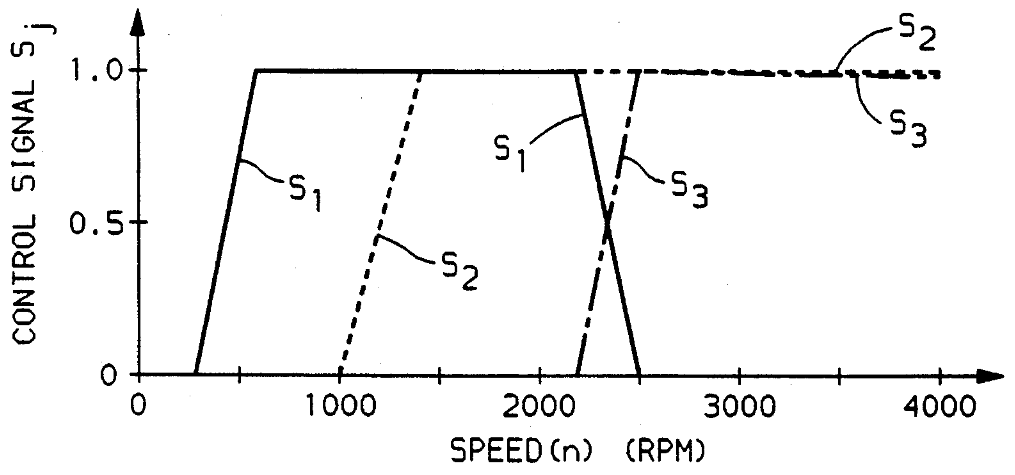
FIG. 7A–C illustrate typical values for control signals produced by the filter controller in the model shown in FIG. 6 as a function of the rotational speed and/or acceleration of the engine when canceling exhaust noise.
Figure 7B:
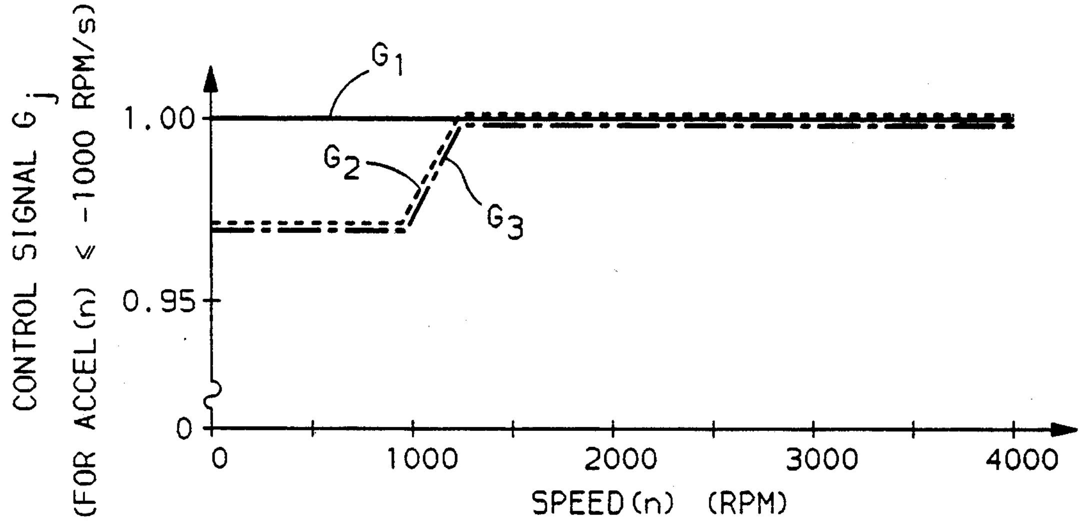
Figure 7C:
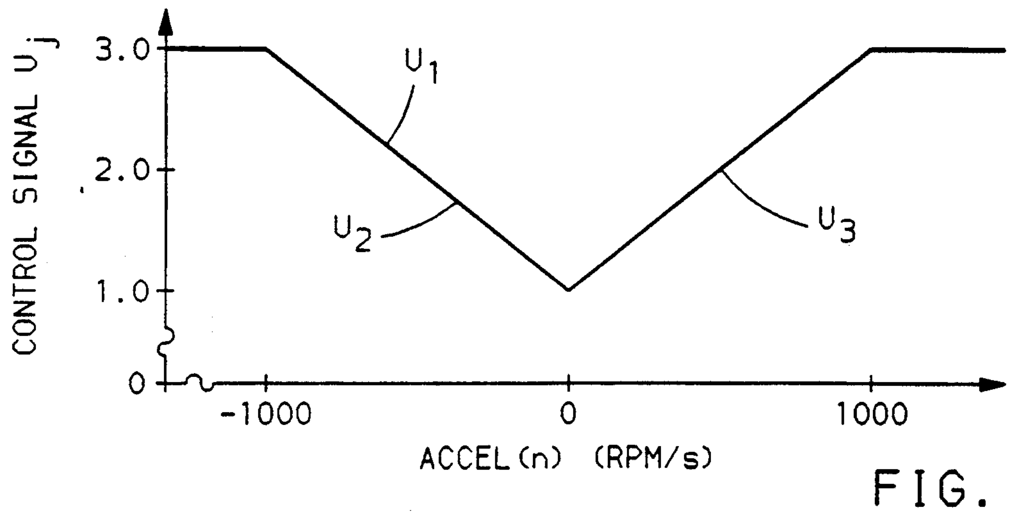

Referring now to FIG. 7(A)-(C), values for the output control signals $S_j$, $U_j$, and $G_j$ provided by filter controller 250 are graphically illustrated as a function of the computed engine SPEED(n) and/or ACCEL(n), with j=1, 2, and 3 as used in the present embodiment.

The values for each control signals $S_j$ shown in FIG. 7A were selected to be correlative with the behavior of the engine noise frequency components that correspond in frequency with the sinusoidal signal components synthesized by each respective signal generator $SG_j$. For example, the engine noise component having a frequency of $4f_0$ was found to have a significant amplitude, essentially when the engine was operated at rotational speeds in the range from 600 to 2200 RPM. Since the control signal $S_1$ is used to scale the amplitude of the output sinusoidal signal from signal generator $SG_1$, which corresponds to this engine noise component at the frequency of $4f_0$, $S_1$ is given a value of 1.0 for rotational speeds in the range from 600 to 2200 RPM, and a value of zero outside this range, except for narrow transitional bands of a few hundred RPM on either side of the 600–2200 RPM range to prevent $S_1$ from shifting too abruptly between the values of zero and one. Likewise, the values for the control signals $S_2$ and $S_3$ in FIG. 7A are selected to follow the behavior of the engine noise components corresponding in frequency with the sinusoidal signal components being synthesized by the signal generators SG2 and SG3, respectively.

This amplitude scaling of the output signals synthesized by the signal generators based upon the rotational speed of the engine was found to significantly improve the ability of the ANC system to attenuate engine noise components that have substantial changes in amplitude with variations in engine rotational speed. This is because the scaled amplitudes of the synthesized sinusoidal signal components entering the adaptive filters from the signal generators now more closely match the amplitude behavior of the actual noise components generated by the engine as it operates at different rotational speeds. As a consequence, the adaptive filters require less time to converge or adapt the filter output signals to achieve a satisfactory attenuation of the engine generated noise.

When engine 10 is operating at rotational speeds above 1200 RPM and the engine rotation is rapidly decelerated at rates≧1000 RPM/second to speeds below 1200 RPM (for example, during closed throttle, heavy vehicle braking), it has been found that the amplitudes of engine noise components having frequencies other than $4f_0$ approach zero very rapidly (in less that one second) Conventional adaptive filters can not respond quickly enough to remove the filter passbands corresponding to these frequencies, and the filter output signals $Y_2(n)$ and Y3(n) will contain signal components having significant amplitudes at these passband frequencies. This will occur even if the actual inputs signals directed to adaptive filters $AF_1$ and $AF_2$ are scaled to zero by control signals $S_1$ and $S_2$ as described above, due to the existence of noise, which passes through the adaptive filters at the passband frequencies. As a result, the observed noise level 22 will actually increase due to the presence of these unnecessary signal components in the canceling waves, since the corresponding engine noise components will have disappeared.

It was recognized that the values of the leakage factor $g_j$ used in the LMS filter adaptation algorithm (see equation (3)) determine the degree to which values of the updated filter weighting coefficients $W_{ij}(n+1)$ are influenced by past values of the weighting coefficients $W_{ij}(n)$ determined during the previous sampling interval. The larger the value of the leakage factor $g_j$, the larger will be the contribution from the past value of a filter weighting coefficient in determining its new updated value, and the more prone the filter is to retaining or remembering its past filtering characteristics. Consequently, by decreasing the leakage factor of adaptive filters $AF_2$ and $AF_3$, during periods of rapid engine deceleration where engine rotational speed drops below 1200 RPM, it was found that the filter passbands associated with the disappearing engine noise components can be eliminated more quickly during the adaptation process.

As indicated in equation (8) and FIG. 6, the adaptive filter leakage factors in the present embodiment are modified by scaling their values in accordance with the control signals $G_j$ produced by the filter controller 250. During normal engine operation, all of the control signals $G_j$ have values of 1.0. However, when filter controller 250 computes an $ACCEL(n) \leqq -1000$ RPM/s, the two control signals $G_2$ and $G_3$ are determined as a function of the computed engine SPEED(n) as shown in FIG. 7B. The value of $G_1$ remains equal to 1.0, since the engine noise component at the frequency $4f_0$ does not disappear during rapid engine deceleration, and consequently, adaptive filter $AF_1$ must retain a passband at the frequency $4f_0$. By determining the values of $G_2$ and $G_3$ in this fashion, and scaling the leakage factors of adaptive filters $AF_2$ and $AF_3$ according to equation (8), it has been found that the adaptive filters can be made to respond more quickly to the disappearance of engine noise components during periods of rapid engine deceleration, thereby significantly enhancing the performance of the ANC system.

It will also be recognized that the above approach can easily be adapted to scale adaptive filter leakage factors in situations where engine noise components are found to quickly disappear with rapid engine acceleration rather than deceleration as described above.

In addition to the above described amplitude fluctuations, the engine noise components, and hence the sinusoidal signal components synthesized by the signal generators, have frequencies that shift in response to variations in engine rotational speeds during abrupt engine acceleration and deceleration. Conventional adaptive filters having fixed convergence factors generally will not be able to accurately track filter input signal components that have rapid frequency fluctuations. This is because filter convergence factors are conventionally fixed at relatively small values, say for example $\mu = 0.01$, to reduce the magnitude of system residual error (the residual noise level represented by the error signal ER(n) in the present embodiment. If the filter convergence factor is increased, to say $\mu = 0.03$, the ability of the adaptive filter to track rapid fluctuations in the frequency of components in the filter input signal will be enhanced, but the magnitude of the system residual error will increase for constant engine speed operation.

It was recognized that the above difficulties could be overcome by providing each adaptive filter with a variable rather than a fixed convergence factor. Since the rate at which signal component frequencies vary depends directly upon the rate of change of the engine rotational speed, i.e. the engine rotational acceleration, the values of the filter convergence factors are made to depend upon the magnitude of the engine rotational acceleration. This is accomplished in the embodiment illustrated in FIG. 6 by the filter controller 250, which generates control signals $U_j$ for scaling the convergence factors of the adaptive filters $AF_j$.

Referring now to FIG. 7C, values for the control signals $U_1$, $U_2$, and $U_3$ are graphically illustrated as a function of the engine acceleration ACCEL(n) computed by the filter controller 250 based upon equation (12). For the present embodiment all of the $U_j$ control signals were made to vary in the same way with changes in ACCEL(n), however, it will be understood that the control signal for each adaptive filter can be made to vary differently with changing engine acceleration and that the values presented in FIG. 7C are merely exemplary for the exhaust noise application.

When the engine operates at constant rotational speeds (ACCEL(n)=0), the frequencies of the engine noise components remain stationary, so it is generally more important to assure that system residual error is a small as possible, rather than to achieve a rapid rate of filter convergence. On the other hand, when the engine is accelerating or decelerating, the frequencies of the engine noise components change rapidly, and it is more important to assure that the filter has rapid rate of convergence.

Recall from equation (9) that the adaptive filter convergence factors in the present embodiment are given by $\mu_j = U_j \mu_{0j}$, where the control signals $U_j$ effectuate a scaling of the corresponding fixed values for $\mu_{0j}$, which in the present embodiment are given by $\mu_{01} = 0.001$, and $\mu_{02} = \mu_{03} = 0.01$. In view of the foregoing, the $U_j$ control signals are given values of 1.0 (see FIG. 7C) to provide the adaptive filters with relatively small values for the convergence factors, when the rotational speed of the engine is stationary, (ACCEL(n)=0). For rapid engine acceleration or deceleration where $ACCEL(n) \geqq 1000$ RPM/s or $ACCEL(n) \leqq -1000$ RPM/s, the control signals $U_j$ are given values of 3.0, to provide the adaptive filters with relatively larger convergence factors and increased rates of convergence. As shown, the values of the control signals $U_j$ increase linearly from 1.0 to 3.0 as engine acceleration or deceleration increases from zero up to 1000 RPM/s. Scaling the adaptive filter convergence factors so that they vary in value as a function of engine acceleration in the above described fashion, significantly enhances the ability of each adaptive filter to track frequency fluctuations in filter input signal components caused by variation in engine rotational speed.

The control signals $S_j$, $G_j$, and $U_j$ in FIG. 7A-C were shown to vary as piecewise linear functions of either engine speed or acceleration. It will be recognized that these representations for the control signals were merely exemplary and that other linear or non-linear representations could just as easily be used. It will also be understood that different forms of noise and/or noise generated by different types of engine will generally have characteristics that differ from those described above, but the control techniques can still be applied to these application by selecting the appropriate values for the control signals based upon the principles set forth above.

Figure 8:
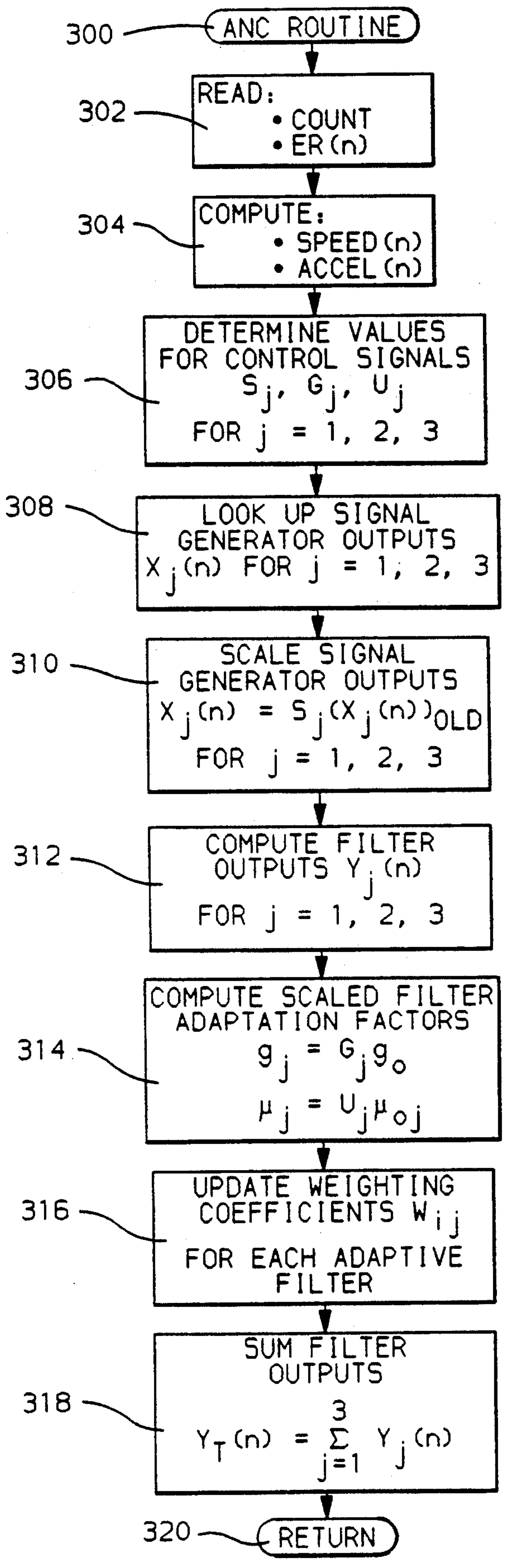
FIG. 8 is a flow diagram representative of the steps executed by a routine programmed into the digital signal processor to perform the signal generating, adaptive filtering, and control functions of the model configuration shown in the FIG. 6.

Referring now to FIG. 8, there is shown a flow diagram representative of the program steps executed by the DSP 52 in performing the parallel signal generating, adaptive filtering, and controlling functions indicated by the block diagram of FIG. 6. The ANC Routine is entered at point 300, after each system interrupt associated with the sampling rate of the DSP 52. It will be understood that prior to the first pass through the ANC Routine, the appropriate variables, timers, counters, etc. will have been initialized to the proper starting values. From point 300, the program proceeds to step 302, where the values of the input signal COUNT and digitized error signal ER(n) are read.

Next at step 304, values for the current engine speed SPEED(n) and acceleration ACCEL(n) are computed according to equations (11) and (12) as described previously.

The routine then proceeds to step 306 where values for the control signals $S_j$, $G_j$, and $U_j$, for j=1, 2, and 3 are determined based upon the computed values for the engine speed SPEED(n) and/or acceleration ACCEL(n) found at step 304. This is accomplished by either computing values for the control signals based upon stored sets of coefficients for empirical equations representing the piecewise linear functional relationships shown in FIG. 7A–C; or by providing stored look up tables containing values for the control signals based upon engine speed an/or acceleration as indicated in FIG. 7A–C. Note the values of the control signals $G_2$ and $G_3$ are less than 1.0 and vary with engine speed as shown in FIG. 7B, only when the computed engine acceleration ACCEL(n)≦−1000 RPM/s. Consequently, the control signals $G_1$, $G_2$, and $G_3$ are given the values of 1.0, and the routine reduces these values for $G_2$ and $G_3$ in accordance with SPEED(n) as shown in FIG. 7B, only after first determining that the computed ACCEL(n)≦−1000 RPM/s.

Once the appropriate values for the control signals are either computed or looked up at step 306, the routine proceeds to step 308 where the sampled amplitude value $X_j(n)$ for each generator output signal (j=1, 2, and 3) is derived (or looked up) in a respective predetermined schedule of stored values based upon the current value of the reference input signal COUNT found previously at step 302.

The stored values for each signal generator schedule are determined from equation (1) by summing the appropriate sinusoidal terms selected to be synthesized by each signal generator over the range of different values for COUNT. Recall that the particular sinusoidal signal components synthesized by each signal generator in the present embodiment were selected as described previously in the specification. After determining a set of values for a particular generator in this fashion, the values are usually normalized to range between −1 and 1 prior to storage in their respective look up schedule. This is achieved by dividing each value in the set by the magnitude of the value found to be largest in the set.

After completing step 308, the routine passes to step 310, where the amplitude of each signal generator output signal is scaled. This is accomplished by multiplying the digital amplitude values produced by each signal generator, represented here as $X_j(n)_{OLD}$, by the value for the corresponding control signal $S_j$ determined at step 306. The product $S_j\ X_j(n)_{OLD}$ then replaces the previous value for $X_j(n)$ stored in memory.

Next at step 312, the filtered output signal $Y_j(n)$ for each adaptive filter $AF_j$ (j=1, 2, and 3) is computed according to equation (2), with the filter input signal being the sequence of digital values stored in the designated memory locations for jth signal generator output $X_j(n-i)$, where in the present embodiment i=0, 1, . . . , and 63, since the adaptive filters have sixty-four taps. Note that each value in the stored sequence represented by $X_j(n-i)$ will have been amplitude scaled, due to the presence of step 310 in the routine.

At step 314, the leakage and convergence factors, $g_j$ and $\mu_j$, employed in the adaptation algorithm of each adaptive filter are modified by scaling their values according to equations (8) and (9) using the values of the control signals $G_j$ and $U_j$ found previously at step 306.

Then at step 316, updated values for the weighting coefficients $W_{ij}(n+1)$ for each adaptive filter $AF_j$ (for j=1, 2, and 3) are computed according to equation (3) using the modified values for the leakage and convergence factors $g_j$ and $\mu_j$ found at step 314 above. These updated values for the filter weighting coefficients are the ones that will be used at step 312 during the next pass through the routine (next sampling interval) to compute new values for the digital filter output signals.

From step 316, the routine proceeds to step 318, where the individual values for the filter output signals $Y_j$ are summed or added together to produce a digital sample for the final output noise canceling signal $Y_T(n)$.

After completing step 318, the routine is exited at step 320. It will be understood that the above ANC ROUTINE is repeatedly executed by the DSP 52 after each sampling interrupt to generate a successive sample values for the digital noise canceling signal $Y_T(n)$ for output by the DSP 52.

As describe above, the ANC ROUTINE implements the particular configuration shown in FIG. 6, which comprises three signal generators and their corresponding paired adaptive filters connected in parallel to signal summer, with the operation of each signal generator and adaptive filter under the direct control of the filter controller. It will be understood that the flow chart for the ANC ROUTINE is equally applicable when implementing the general parallel signal generator and paired adaptive filter configuration of FIG. 3, which does not include the filter controller or its scaling functions. In this case, the integer variable j would be allowed to have integer values ranging from 1 to J, the leakage and convergence factors for each adaptive filter would be assigned fixed values, and steps 304, 306, 310, and 314 would be removed from the ANC ROUTINE. Thus, those advantages provided by the parallel filtering configuration and the separation of sinusoidal components having frequencies corresponding to those of adjacent noise frequencies for synthesis by different signal generators can be realized without implementing the filter controller functions.

It will also be recognized that the filter controller 250 provides three different types of control signals $S_j$, $G_j$, and $U_j$ to each signal generator and corresponding paired adaptive filter in the parallel configuration shown in FIG. 6. Each type of control signal performs a separate and distinct function that provides advantages or benefits different and apart from those provided by the other types of control signals. Consequently, it will be understood that each control function can be implemented either individually, or in combination with any of the other control functions in the ANC ROUTINE by simply removing or adding the appropriate scaling operations at steps 310 and 314. It will also be understood that these control functions can be applied to a single signal generator and its correspondingly paired adaptive filter, by setting j=1, or to any number of parallel signal generators and correspondingly paired adaptive filters by merely permitting j to have larger integer values.

In the foregoing description, the preferred form for each adaptive filter in the ANC system has been the filtered-X configuration, with the adaptation or updating of filter weighting coefficients achieved by use of the leaky LMS algorithm. Other types of adaptive filter configurations and updating algorithms are known and used by those skilled in the art of ANC, and it will be recognized that the principles underlying the above embodiments will be equally applicable to other types of ANC systems having different adaptive filter configurations and updating algorithms. For example, the equivalent leakage and/or convergence factors in any type of filter updating algorithm can be scaled in accordance with changes in engine rotational speed and/or acceleration to improve the adaptive filter response to such changes Also, the amplitude of any input signal representing the engine noise to be canceled by an ANC system can be scaled as a function of engine rotational speed to make the input signal more representative of the behavior of the amplitude of the noise as engine rotational speed changes.

Therefore, the aforementioned description of the preferred embodiments of the invention is for the purpose of illustrating the invention, and is not to be considered as limiting or restricting the invention, since many modifications may be made by the exercise of skill in the art without departing from the scope of the invention.

The embodiments of the invention in which an exclusive property or privilege is claimed are defined as follows:

1. A system for attenuating undesirable noise generated by an internal combustion engine, wherein the undesirable noise contains at least one sinusoidal noise component having an amplitude and frequency that vary in accordance with engine rotational speed, the system comprising:
- means for sensing engine rotational speed;
- means responsive to said engine rotational speed for generating a generator output signal containing at least one sinusoidal signal component, where each sinusoidal signal component has a predetermined constant amplitude, and a frequency corresponding to the frequency of a respective sinusoidal noise component;
- means for producing a control signal having an amplitude that varies as a function of the sensed engine rotational speed;
- means for multiplying the generator output signal with the control signal to produce a filter input signal;
- an adaptive filter having adjustable filtering characteristics for filtering the filter input signal to produce a filter output signal;
- actuator means for generating noise canceling waves in response to the filter output signal and for superimposing the generated noise canceling waves with the undesirable noise;
- means for sensing a residual noise level resulting from the superposition of the noise canceling waves and the undesirable noise and for developing an error signal representative of the residual noise level; and
- means for adaptively adjusting the filtering characteristics of the adaptive filter based upon the error signal to reduce the sensed residual noise level.

2. A system for attenuating undesirable noise generated by an internal combustion engine, wherein the undesirable noise contains at least one sinusoidal noise component having an amplitude and frequency that vary in relation to the time rate of change of engine angular rotational position in an engine operating cycle, the system comprising:
- means for sensing the engine angular rotational position in the operating cycle;
- means for deriving engine rotational speed by determining the time rate of change of the angular rotational position of the engine in the operating cycle;
- means responsive to said engine rotational speed for generating a generator output signal containing at least one sinusoidal signal component, where each sinusoidal signal component has a predetermined constant amplitude, and a frequency corresponding to the frequency of a respective sinusoidal noise component, wherein the generator output signal is derived from predetermined schedule of values based upon the sensed angular rotational position of the engine in the operating cycle;
- means for producing a control signal having a varying amplitude that is obtained from a look up table based upon the derived engine rotational speed;
- means for multiplying the generator output signal with the control signal to produce a filter input signal;
- an adaptive filter having adjustable filtering characteristics for filtering the filter input signal to produce a filter output signal;
- actuator means for generating noise canceling waves in response to the filter output signal and for superimposing the generated noise canceling waves with the undesirable noise;
- means for sensing a residual noise level resulting from the superposition of the noise canceling waves and the undesirable noise and for developing an error signal representative of the residual noise level; and
- means for adaptively adjusting the filtering characteristics of the adaptive filter based upon the error signal to reduce the sensed residual noise level.

3. A system for attenuating undesirable noise generated by an internal combustion engine, wherein the undesirable noise contains multiple sinusoidal noise components each having an amplitude and a frequency that vary in accordance with engine rotational speed, the system comprising:
- means for sensing engine rotational speed;
- signal generating means responsive to said engine rotational speed for producing a plurality of generator output signals, where each generator output signal contains at least one sinusoidal signal component with each sinusoidal signal component having a predetermined constant amplitude and a frequency corresponding to a respective one of the sinusoidal noise components;
- means for producing a plurality of control signals each control signal having a varying amplitude determined in accordance with a respective predetermined function based upon the sensed engine rotational speed;
- means for multiplying each generator output signal with a respective one of the control signals to produce a corresponding filter input signal;
- a plurality of adaptive filters, each adaptive filter having adjustable filtering characteristics for filtering a respective one of the filter input signals to produce a corresponding filter output signal;
- summing means for adding one filter output signal to produce an output canceling signal;
- actuator means for generating noise canceling waves in response to the output canceling signal and for superimposing the canceling waves with the undesirable noise;
- means for sensing a residual noise level resulting from the superposition of the canceling waves and the undesirable noise and for developing an error signal indicative of the residual noise level; and means for adaptively adjusting the filtering characteristics of each one of the adaptive filters in accordance with the error signal to reduce the sensed level of residual noise.

4. The system of claim 3, wherein the signal components contained in the generator output signals are partitioned according to the amplitude behavior of their corresponding noise components with respect to engine rotational speed, and the respective predetermined function for each control signal is correlative with the amplitude behavior of those noise components corresponding to the signal components contained in the generator output signal that is multiplied by the resepective control signal.

5. A system for attenuating undesirable noise generated by an internal combustion engine, wherein the undesirable noise contains multiple sinusoidal noise components having amplitudes and frequencies that vary in relation to the time rate of change of engine angular rotation position in an engine operating cycle, the system comprising;

means for sensing the engine angular rotational position in the engine operating cycle;

means for sensing the engine angular rotational position in the engine operating cycle;

means for deriving engine rotational speed by determining the time rate of change of the sensed angular rotational position of the engine in the operating cycle;

means for producing a plurality of generator output signals, where each generator output signal contains at least one sinusoidal signal component, with at least one generator output signal containing multiple sinusoidal signal components, and each sinusoidal signal component having a constant predetermined amplitude and a frequency corresponding to the frequency of a respective one of the sinusoidal noise component, and with each generator output signal being derived from respective predetermined schedule of values based upon the sensed angular rotational position of the engine in the operating cycle;

means for producing a plurality of control signals, each control signal having a varying amplitude determined in accordance with a respective predetermined function based upon the derived rotational speed of the engine;

means for multiplying each generator output signal with a respective one of the control signals to produce a corresponding filter input signal;

a plurality of adaptive filters, each adaptive filter having adjustable filtering characteristics for filtering a respective one of the filter input signals to produce a corresponding filter output signal;

summing means for adding each filter output signal to produce an output canceling signal;

actuator means for generating noise canceling waves in response to the output canceling signal and for superimposing the canceling waves with the undesirable noise;

means for sensing a residual noise level resulting from the superposition of the canceling waves and the undesirable noise and for developing an error signal indicative of the residual noise level; and means for adaptively adjusting the filtering characteristics of each one of the adaptive filters in accordance with the error signal to reduce the sensed level of residual noise.

6. The system of claim 5, wherein multiple signal components contained in any generator output signal is selected so that the amplitude behavior of their corresponding noise components behave similarly with respect to engine rotational speed, and the respective predetermined function for each control signal is correlative with the amplitude behavior of those noise components corresponding to the signal components contained in the generator output signal that is multiplied by the respective control signal.

* * * * *